United States Patent
Palese

[11] Patent Number: 5,318,029
[45] Date of Patent: Jun. 7, 1994

[54] TONOMETER SHIELD

[75] Inventor: Millie Palese, El Segundo, Calif.

[73] Assignee: Oasis Medical, Inc., Glendora, Calif.

[21] Appl. No.: 835,728

[22] Filed: Feb. 11, 1992

[51] Int. Cl.⁵ .............................................. A61B 3/16
[52] U.S. Cl. ................................ 128/652; 374/209; 128/736
[58] Field of Search .................... 128/645–652, 128/736; 604/263; 206/305, 306, 316.1, 363, 438; 374/158, 209

[56] References Cited

U.S. PATENT DOCUMENTS

| | | | |
|---|---|---|---|
| 4,200,110 | 4/1980 | Peterson et al. | 128/634 |
| 4,573,981 | 3/1986 | McFarlane | 604/263 |
| 4,599,901 | 7/1986 | Hirschfield | 128/634 |
| 4,662,360 | 5/1987 | O'Hara et al. | 128/736 |
| 4,784,149 | 11/1988 | Berman et al. | 374/158 |
| 4,880,413 | 11/1989 | Giuffre et al. | 604/263 |
| 4,922,914 | 5/1990 | Segal et al. | 128/646 |
| 4,948,062 | 8/1990 | Mahar et al. | 128/645 |
| 5,002,057 | 3/1991 | Brady | 128/652 |
| 5,031,622 | 7/1991 | LaHaye | 128/646 |
| 5,078,692 | 1/1992 | Cuprak | 604/263 |
| 5,088,834 | 2/1992 | Howe et al. | 128/736 |

FOREIGN PATENT DOCUMENTS 2220354 1/1990 United Kingdom .............. 604/263

Primary Examiner—Randy C. Shay
Attorney, Agent, or Firm—Michael J. Ram

[57] ABSTRACT

A shield for use with an applanation tonometer wherein a light activated material is incorporated into or onto the shield. In one version, the shield comprises a tubular cover with one closed end and one open end, a flared skirt attached to the open end and a flange attached to the skirt at its widest dimension. A particular design has the closed end curved inward.

7 Claims, 3 Drawing Sheets

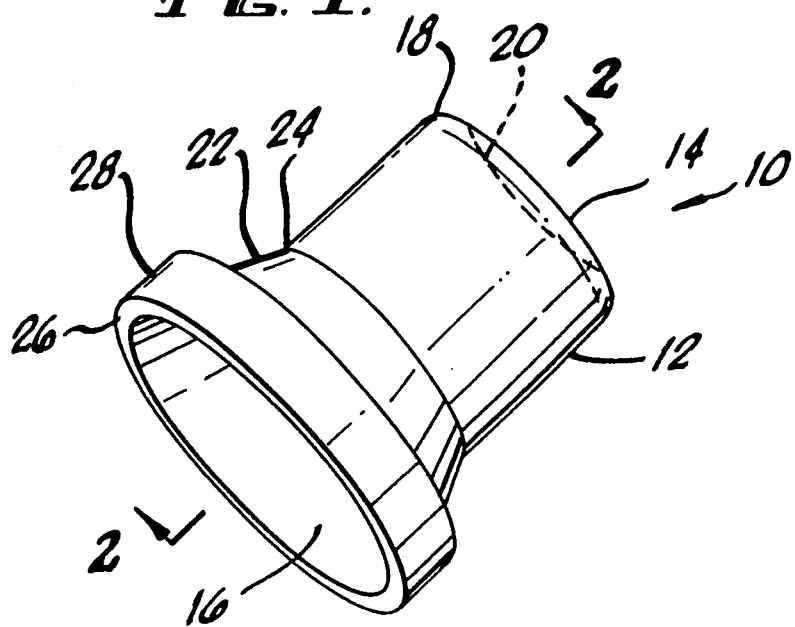
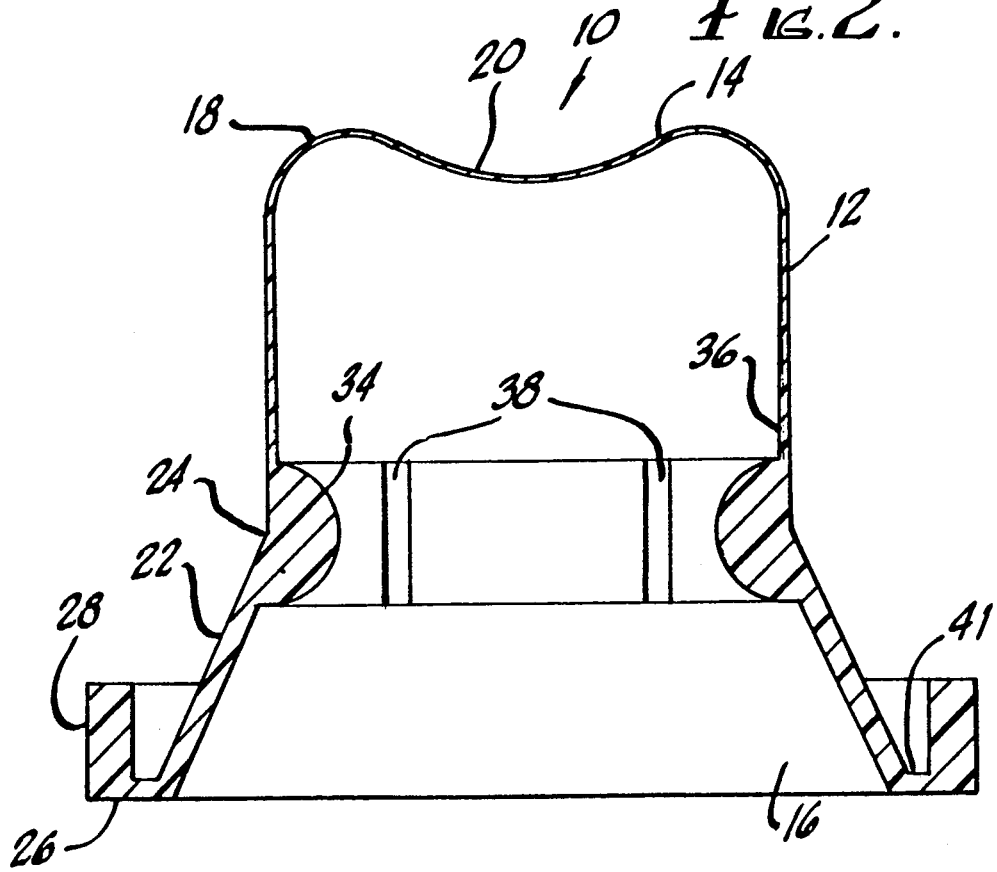

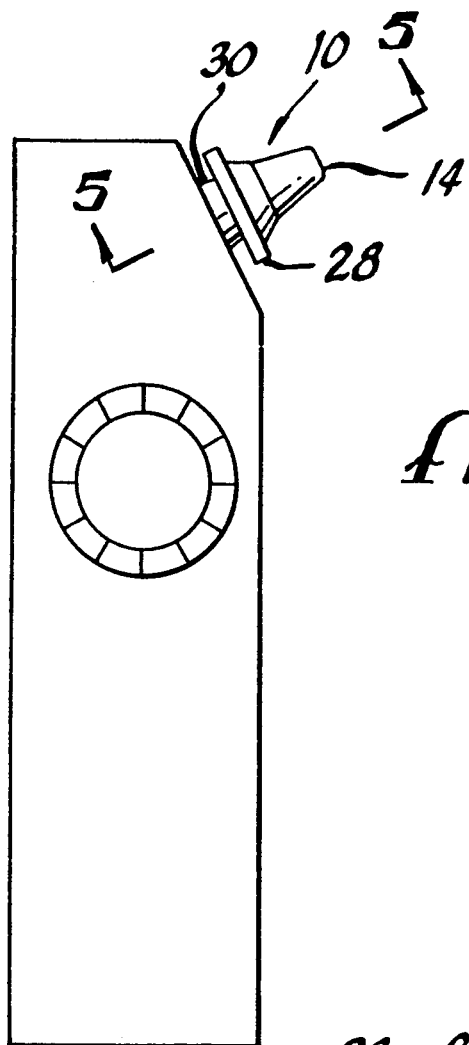
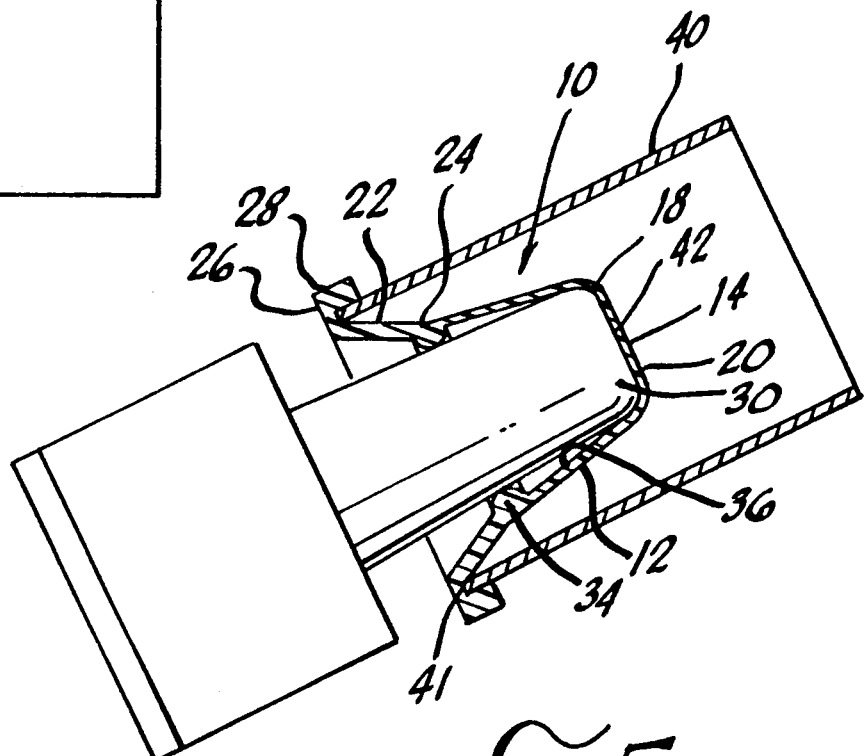

TONOMETER SHIELD

BACKGROUND

The present invention relates to a shield to be applied to a mechanical device for measuring the pressure within a human eye which, at the same time, improves the ability of the operator to make accurate pressure determinations.

The internal pressure in the human eye is usually determined through the use of a tonometer. A common type of tonometer is the applanation tonometer which determines internal pressure as a function of corneal flattening. In applanation tonometry the tip of the tonometer is brought into contact with the outer surface of the cornea. Applanation pressure is measured as the surface of the cornea is flattened to a predetermined point. If the eye has a normal internal pressure the applanation pressure required is within a predetermined range. As the internal pressure of the eye increases, the applanation pressure must be increased to obtain the same area of cornea flattening.

One type of applanation tonometer which is believed to give relatively accurate pressure readings is the Goldmann tonometer. To use the Goldmann tonometer a local anesthetic and then fluorescein is applied to the corneal surface. When the eye is exposed to blue light the fluorescein imparts a bright greenish yellow glow to the corneal surface. When the tonometer tip is applied to the outer surface of the eye two bright yellow green semicircular arcs are visualized. As the tip is advanced toward the eye, flattening the cornea, the arcs move across the visual field. Forward movement of the tonometer is continued until the desired end point image is obtained (the inner edge of the upper arc is aligned with the inner edge of the lower arc). The reading on the tonometer is then converted to give the internal pressure of the eye.

While there can be several causes for erroneous readings in use of the Goldmann tonometer, a common source of error is the use of too much or too little fluorescein or dilution of the fluorescein previously applied by excessive tearing. This variation in fluorescein can cause the operator to obtain pressure readings which are either higher or lower than the actual pressure, thus resulting in improper treatment for glaucoma or other causes of elevated pressure.

Besides applanation tonometers, ophthalmic pressures are also determined by using devices incorporating a pressure transducer. These tonometers usually require a cover to prevent moisture from entering the transducer. Additionally, other ophthalmic measuring devices applied to the eye, such as a biometric ruler, include an ultrasonic transducer. These ultrasonic transducers require a cover to retain a film of water against the ultrasonic tip of the device in order to obtain a reading.

Shields have not been effectively used on applanation tonometers as they can interfere with the proper functioning of the device, the obtaining of correct pressure readings, by reducing the visibility of the yellow-green semicircular arcs derived from placing fluorescein on the eye. However, there is a significant concern regarding the transfer of infections from the eye of one patient to a second patient's eye as a result of inadequate disinfecting of the device. This has been resolved to some extent by the application of a disposable, flexible cover over the tip of tonometers utilizing a pressure or an ultrasonic transducer.

Thus, there is a need for a simple, accurate and reproducible method for applying the fluorescein to the eye. Additionally, there is a need for means to prevent transfer of infectious agents from one patient to another while obtaining pressure or other measurements on the eye.

SUMMARY

These needs are met by a polymeric shield embodying features of the present invention.

The polymeric shield of the present invention comprises a flexible cover for placement over the tip of an ophthalmic instrument. When used on an applanation tonometer the shield can include a light activated material incorporated into or onto the material used to form the cover.

In a specific embodiment of the shield, the device comprises a tubular cover having a closed end and an open end, the closed end being sized to fit over the sensing end of the tonometer tip. The open end of the cover incudes a flared skirt and a flange, the flange being shaped to receive a placement sleeve. The light activated material incorporated into the flexible material forming the cover is fluorescein.

The shield prevents transference of infectious agents from patient to patient. The addition of the light activated material eliminates the need to apply fluorescein to the patient's eye, improves the accuracy and reproducibility of pressure measurements made with the applanation tonometer since a predetermined amount of light activated material is contained in or on the shield, and makes it easier for the operator to make pressure measurements.

DRAWINGS

These and other features, aspects, and advantages of the present invention will become better understood with reference to the following description, appended claims, and accompanying drawings, where:

FIG. 1 is a perspective side view of the tonometer shield of the invention.

FIG. 2 is a cutaway side view of the tonometer shield of FIG. 1 taken along line 2—2 of FIG. 1.

FIG. 4 is a side view of the tonometer shield of FIG. 1 applied to an applanation tonometer.

FIG. 5 is a cutaway side view of the tonometer shield of FIG. 1 applied to a tonometer tip taken along line 5—5 of FIG. 4.

DESCRIPTION

Figure 3:
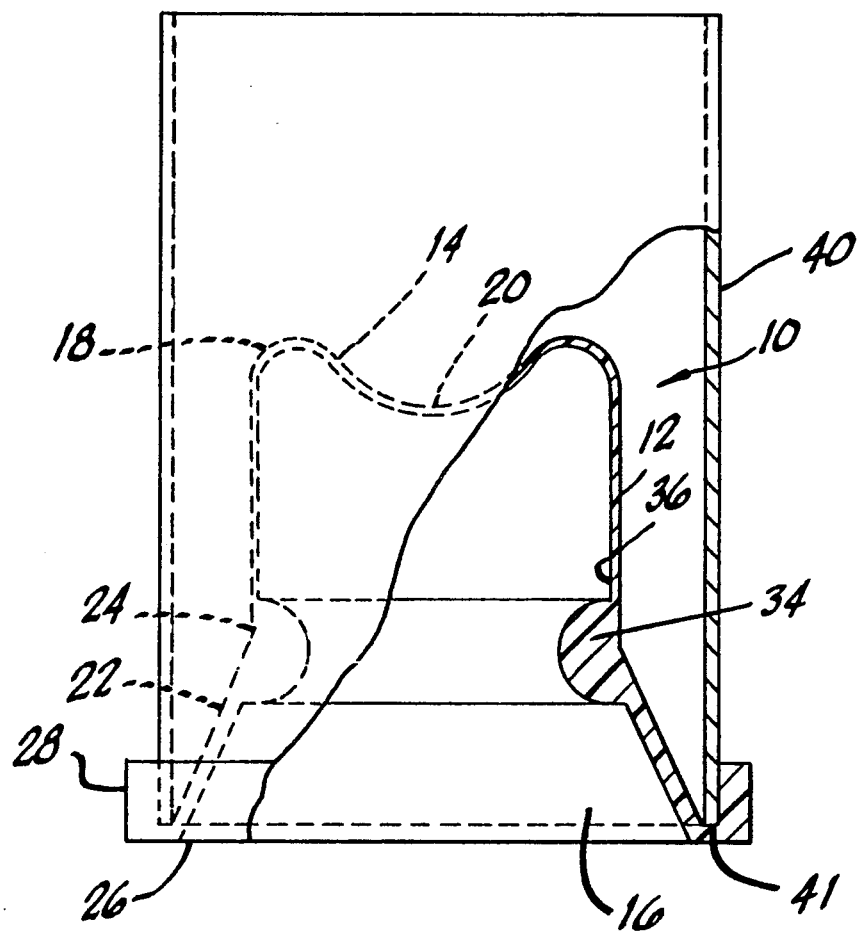
FIG. 3 is a partially cutaway view of the tonometer shield of FIG. 1 with a placement tube placed over the shield.

FIGS. 1 through 5 show versions of the tonometer shield 10 embodying features of the present invention.

The tonometer shield 10 comprises a tubular portion 12 with a closed end 14 and an insertion end 16. In a preferred embodiment the closed end 14 has a raised circumferential edge 18 and an indented center 20. Attached to the insertion end 16 of the shield 10 is a flared skirt 22, the skirt 22 having an external diameter at the point of attachment 24 to the tubular portion 12 equal to that of the outer diameter of the tubular portion 12 and a diameter at the bottom 26 of the skirt greater than the diameter at the point of attachment 24. Attached to the skirt bottom 26 is a flange 28 which surrounds and is spaced from at least a portion of the skirt 22.

The internal diameter of the tubular portion 12 is selected so that it is greater than the outer diameter of the tonometer tip 30 it is designed to cover. The shield 10 shown in the Figures includes a retaining ring 34 extending from the internal wall 36 at the point of attachment 24 between the tubular portion 12 and the skirt 22. During insertion the retaining ring 34 is stretched around the tonometer tip and holds the shield in place. Traversing the retaining ring 34 are one or more vents 38 to allow trapped air to escape during application. However, other means can be used to hold the shield to the tonometer. For example, a groove can be formed in the outer surface of the shield for the application of a band or elastic member. Alternatively the inner and outer surface of the shield can be smooth and a clamping mechanism can be used to hold the shield to the tonometer tip 30.

To aid in placing the shield 10 on a tonometer tip 30 and to protect the shield 10 from contamination or damage during application, a sleeve 40 is placed over the tubular portion 12, one end of the sleeve 40 resting in the space 41 between the flange 28 and the skirt 22 as shown in FIG. 3. To use the shield 10, the flange end of the shield 10 and sleeve 40 combination is placed over the tonometer tip 30. The sensing end 42 of the tonometer tip 30 first makes contact with the indented center 20 of the shield 10. Further insertion of the tip 30 causes the indented center to extend laterally beyond the circumferential edge 18. The tip 30 is further inserted into the shield 10 until the retaining ring 34 fits snugly on the tip 30. Air enclosed within the shield 10 escapes through the vents 38 in the retaining ring 34 as the shield 10 is applied to the tonometer tip 30.

The shield 10 can be prepared from various different flexible or elastic polymers such as silicone rubber, natural or synthetic rubber, thermoplastic elastomers such as polyurethanes or butadiene-styrene copolymers, or thermoplastic polymers such as polyethylene or polypropylene. The main criteria for selecting the material is that it is flexible, has at least a small amount of elasticity, and that the material is not easily torn or ruptured under stress. For shields used over an applanation tonometer, the material, for best visualization of the semi-circles, should be clear. A suitable material for the sleeve is cardboard or any stiff plastic, such as polyethylene or polypropylene.

The exact dimensions and shape of the shield 10 depends on the particular tonometer it is designed to fit. However, a typical shield has a thickness of about 0.003 inch at the indented center 20, the tubular portion 12 has a diameter of about 0.37 inch, and a length of about 0.28 inch, and the skirt portion is about 0.18 inch in length, the diameter at the wide end of the skirt is about 0.52 inch, and the skirt wall thickness is about 0.015 inch. A sleeve typically has a wall thickness of about 0.17 inch, an outer diameter of about 0.58 and a length of at least about 0.8 inch.

In a particular embodiment of the shield 10 a light activated material is incorporated into or onto the material forming the shield. Incorporating the material into the shield or between the shield and the tonometer greatly reduces the possibility that the material could cause an allergic or toxic reaction in the eye or that the amount of material will vary over time. Therefore, various material which, in the past, would not have been considered suitable for use in enhancing the readability of an applanation tonometer can now be considered as suitable when incorporated into or onto the shield. Suitable light activated materials can be fluorescein, derivatives of fluorescein such as water soluble fluorescein salts, other light activated chemicals, or light activated minerals such as zinc sulfide. The light activated material can be blended with the shield material prior to forming the shield, can be dried onto the surface of the shield, can be chemically bound to the shield material prior to or after forming the shield, or can be absorbed or adsorbed onto or into the shield once the shield is formed.

Where fluorescein or a fluorescein derivative is the light activated material blended with the polymer, the desired concentration of active material in the final product is from 40 ppm to 4000 ppm, depending on the thickness of the shield and the derivative of fluorescein used with a more preferred range being from 200 to 2000 ppm. This can be obtained by dissolving the fluorescein, or a fluorescein derivative, in a solvent compatible with the polymer and then blending the materials. For example, alcohols or water-alcohol solutions, particularly isopropanol, can be used. Alternately, a solution of light activated materials can be blended with the polymer pellets, chips, solvent solution or melt before forming the shield.

Light active materials can be applied to the inner surface of the shield by drying a solvent solution of the material coated onto the inner surface. The desired concentration of light activated material is 0.005 to 0.05 mg per square centimeter of shield surface. The solvent selected should not destroy the optical clarity of the shield.

To use an applanation tonometer, such as the Goldmann tonometer, a topical anaesthetic is applied to the eye to be tested followed by the application of one or two drops of fluorescein. A blue light is shown on the eye causing the fluorescein to give the surface of the eye a bright greenish-yellow glow. The tonometer sensing tip is then brought forward and into contact with the cornea. The applanation pressure on the cornea is then slowly increased until the desired pattern, i.e., an overlapping of inner edges of two semicircular arcs, the visibility of which has been enhanced by addition of the fluorescein, has been obtained. The amount of applanation pressure applied by the tonometer is then recorded and converted to a measure of the internal pressure of the eye.

The accuracy and reproducibility of the reading can be dependent on the amount of fluorescein on the cornea. Too much fluorescein and the semicircular arcs will be wide and out-of-focus causing an inaccurate reading. Too little fluorescein and the arcs can be too dim to be seen. It has been found that use of a shield over the tonometer tip, where the shield has a consistent amount of fluorescein bound therein, or deposited on the surface between the shield and the tonometer tip results in more reproducible, and thus more accurate, readings without interfering with the operation of the tonometer.

As an added advantage, the shield can be changed each time the tonometer is used on a new patient, thus avoiding transfer of infectious agents from one patient to another. Currently, shields are not used on applanation tonometers because of a belief that the shields interfere with the use of the tonometer when fluorescein is applied to the eye. This presents a dilemma; transfer of infectious agents is of particular concern to both physicians and patients because of the increased spread of AIDS and the prevalence of individuals who are HIV-positive.

A tonometer with shields produced according to the above specification performed as well as or better than a tonometer operated according to standard techniques without the use of a shield.

Although the present invention has been described in considerable detail with reference to certain preferred versions and uses thereof, other versions are possible. For example, light activated materials other than fluorescein can be utilized. Also, various different materials can be used to form the shield. Additionally, while one particular configuration of the shield has been shown, shields of various configurations and dimensions either with or without the light activated material are contemplated by the invention. Still further the invention is not limited to shields for application to an applanation tonometer. The cover can be applied to other types of ophthalmic measuring devices and covers containing light activated materials may be used in various different applications where the light sensitive nature of the additive enhances functioning of the device to which it is applied. Therefore, the spirit and scope of the appended claims should not be limited to the description of the preferred versions contained herein.

What is claimed is:

1. A shield for application to an applanation tonometer, the shield comprising:
   a tubular portion having a placement end on a first extremity thereof and a displaceable closed end on the second extremity thereof, the displaceable closed end of the shield having a center portion which is initially curved towards the placement end of the tubular portion,
   wherein the tubular portion includes a raised ring attached to the inner surface of the shield to hold the shield to the tonometer, the raised ring having vents therethrough to allow the escape of trapped air,
   a flared skirt attached to the placement end of the tubular portion, the flared skirt increasing in diameter from the point of attachment to the tubular portion, the skirt terminating in a flange, and
   the flange surrounding and extending over at least a portion of the skirt, said flange adapted to receive a placement sleeve,
   the shield being formed from a substantially transparent, flexible material.

2. The shield of claim 1 which further includes a removable sleeve having a first end sized to fit between the flange and the skirt at the junction of the skirt and flange, the length of the sleeve being chosen so that the sleeve extends from the junction of the skirt with the flange to a point beyond the closed end of the tubular portion.

3. The shield of claim 1 further having a light activated material bound to the substantially transparent, flexible material.

4. The shield of claim 3 wherein the light activated material is fluorescein.

5. The shield of claim 4 wherein the fluorescein is incorporated in the flexible material.

6. The shield of claim 4 wherein the fluorescein is coated onto a surface of the closed end of the tubular portion.

7. The shield of claim 1 wherein the flexible material is a light activated material.

* * * * *